(12) United States Patent
Tuval et al.

(10) Patent No.: US 11,039,915 B2
(45) Date of Patent: Jun. 22, 2021

(54) BLOOD VESSEL TUBE

(71) Applicant: MAGENTA MEDICAL LTD., Kadima (IL)

(72) Inventors: Yosi Tuval, Even Yehuda (IL); Ehud Schwammenthal, Ra'anana (IL); Daniel Glozman, Kfar Yona (IL); Gad Lubinsky, Ein Vered (IL)

(73) Assignee: MAGENTA MEDICAL LTD., Kadima (IL)

(*) Notice: Subject to any disclaimer, the term of this patent is extended or adjusted under 35 U.S.C. 154(b) by 58 days.

(21) Appl. No.: 16/335,786

(22) PCT Filed: Sep. 28, 2017

(86) PCT No.: PCT/IL2017/051092
§ 371 (c)(1),
(2) Date: Mar. 22, 2019

(87) PCT Pub. No.: WO2018/061002
PCT Pub. Date: Apr. 5, 2018

(65) Prior Publication Data
US 2019/0239998 A1 Aug. 8, 2019

Related U.S. Application Data

(60) Provisional application No. 62/401,403, filed on Sep. 29, 2016.

(51) Int. Cl.
*A61F 2/07* (2013.01)
*A61F 2/06* (2013.01)
(Continued)

(52) U.S. Cl.
CPC .............. *A61F 2/07* (2013.01); *A61B 5/0215* (2013.01); *A61B 5/4836* (2013.01);
(Continued)

(58) Field of Classification Search
CPC .................. A61F 2/07; A61F 2002/068; A61F 2002/061; A61F 2002/018; A61F 2/2475
See application file for complete search history.

(56) References Cited

U.S. PATENT DOCUMENTS 4,919,647 A    4/1990  Nash
4,954,055 A    9/1990  Raible et al.
(Continued)

FOREIGN PATENT DOCUMENTS

AU    2013205145 A1    5/2013
CN       1219136 A     6/1999
(Continued)

OTHER PUBLICATIONS

Communication for European Application No. 15753493.4 dated Jul. 17, 2019.
(Continued)

*Primary Examiner* — Suba Ganesan
(74) *Attorney, Agent, or Firm* — Dorsey & Whitney LLP

(57) ABSTRACT

Apparatus and methods are described including a tube (20) that defines a flared downstream portion (30) that diverges toward a downstream end (32) of the tube, and a flared upstream portion (26) that diverges toward an upstream end (28) of the tube, such that a central portion (34) of the tube is narrower than at the ends of the tube. The tube defines a plurality of lateral openings (36). A support frame (24) supports the tube within a subject's vena cava, such that the downstream portion is sealed with respect to the wall of the vena cava downstream of junctions of the vena cava with all of the subject's renal veins, and the upstream portion is sealed with respect to the inner wall of the vena cava upstream of junctions of the vena cava with all of the subject's renal veins. Other applications are also described.

25 Claims, 6 Drawing Sheets

(51) Int. Cl.
*A61B 5/0215* (2006.01)
*A61B 5/00* (2006.01)
*A61F 2/48* (2006.01)

(52) U.S. Cl.
CPC .............. *A61B 5/6862* (2013.01); *A61F 2/06* (2013.01); *A61F 2002/068* (2013.01); *A61F 2002/482* (2013.01); *A61F 2210/0014* (2013.01); *A61F 2230/001* (2013.01); *A61F 2250/001* (2013.01); *A61F 2250/0039* (2013.01)

(56) References Cited

U.S. PATENT DOCUMENTS

| | | |
|---|---|---|
| 5,613,935 A | 3/1997 | Jarvik |
| 5,713,730 A | 2/1998 | Nose et al. |
| 5,749,855 A | 5/1998 | Reitan |
| 5,772,693 A | 6/1998 | Brownlee |
| 5,876,385 A | 3/1999 | Ikari et al. |
| 5,964,694 A | 10/1999 | Siess et al. |
| 6,086,527 A | 7/2000 | Talpade |
| 6,135,729 A | 10/2000 | Aber |
| 6,247,892 B1 | 6/2001 | Kazatchkov et al. |
| 6,482,228 B1 | 11/2002 | Norred |
| 6,533,716 B1 | 3/2003 | Schmutz-Rode et al. |
| 6,592,567 B1 | 7/2003 | Levin et al. |
| 6,616,624 B1 | 9/2003 | Kieval |
| 6,884,210 B2 | 4/2005 | Nose et al. |
| 7,004,925 B2 | 2/2006 | Navia et al. |
| 7,144,364 B2 | 12/2006 | Barbut et al. |
| 7,159,593 B2 | 1/2007 | McCarthy et al. |
| 7,201,772 B2 | 4/2007 | Schwammenthal et al. |
| 7,335,192 B2 | 2/2008 | Keren et al. |
| 7,341,570 B2 | 3/2008 | Keren et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,914,503 B2 | 3/2011 | Goodson et al. |
| 8,012,121 B2 | 9/2011 | Goodson et al. |
| 8,079,948 B2 | 12/2011 | Shifflette |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | Mcbride et al. |
| 8,449,443 B2 | 5/2013 | Rodefeld et al. |
| 8,512,262 B2 | 8/2013 | Gertner |
| 8,538,535 B2 | 9/2013 | Ariav et al. |
| 8,579,858 B2 | 11/2013 | Reitan et al. |
| 8,617,239 B2 | 12/2013 | Reitan |
| 8,690,749 B1 | 4/2014 | Nunez |
| 8,734,331 B2 | 5/2014 | Evans et al. |
| 8,734,508 B2 | 5/2014 | Hastings et al. |
| 8,777,832 B1 | 7/2014 | Wang et al. |
| 8,849,398 B2 | 9/2014 | Evans |
| 9,028,216 B2 | 5/2015 | Schumacher et al. |
| 9,138,518 B2 | 9/2015 | Campbell et al. |
| 9,162,017 B2 | 10/2015 | Evans et al. |
| 9,314,558 B2 | 4/2016 | Er |
| 9,358,329 B2 | 6/2016 | Fitzgerald et al. |
| 9,597,205 B2 | 3/2017 | Tuval |
| 9,764,113 B2 | 9/2017 | Tuval et al. |
| 9,913,937 B2 | 3/2018 | Schwammenthal et al. |
| 10,039,874 B2 | 8/2018 | Schwammenthal et al. |
| 10,231,838 B2 | 3/2019 | Chin et al. |
| 10,245,363 B1 | 4/2019 | Rowe |
| 10,583,231 B2 | 3/2020 | Schwammenthal et al. |
| 10,799,626 B2 | 10/2020 | Siess et al. |
| 2002/0107536 A1 | 8/2002 | Hussein |
| 2003/0055486 A1 | 3/2003 | Adams et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0055082 A1 | 3/2005 | Ben et al. |
| 2005/0079274 A1 | 4/2005 | Palasis et al. |
| 2005/0119682 A1 | 6/2005 | Nguyen et al. |
| 2006/0106449 A1 | 5/2006 | Ben |
| 2007/0100435 A1 | 5/2007 | Case et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0293808 A1 | 12/2007 | Williams et al. |
| 2008/0103591 A1 | 5/2008 | Siess |
| 2008/0132748 A1 | 6/2008 | Shifflette |
| 2008/0154236 A1 | 6/2008 | Elkins et al. |
| 2008/0183280 A1 | 7/2008 | Agnew et al. |
| 2009/0024195 A1 | 1/2009 | Rezai et al. |
| 2009/0062597 A1 | 3/2009 | Shifflette |
| 2009/0093796 A1 | 4/2009 | Pfeffer et al. |
| 2009/0131785 A1 | 5/2009 | Lee et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0130810 A1 | 5/2010 | Mohl |
| 2011/0004046 A1 | 1/2011 | Campbell et al. |
| 2011/0106244 A1 | 5/2011 | Ferrari et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0301662 A1 | 12/2011 | Bar-yoseph et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0116382 A1 | 5/2012 | Ku et al. |
| 2012/0130469 A1 | 5/2012 | Cragg et al. |
| 2012/0172654 A1 | 7/2012 | Bates |
| 2012/0224970 A1 | 9/2012 | Schumacher et al. |
| 2012/0237357 A1 | 9/2012 | Schumacher et al. |
| 2013/0053623 A1 | 2/2013 | Evans et al. |
| 2013/0053732 A1 | 2/2013 | Heuser |
| 2013/0079874 A1 | 3/2013 | Doss et al. |
| 2013/0177409 A1 | 7/2013 | Schumacher et al. |
| 2013/0177432 A1 | 7/2013 | Toellner et al. |
| 2014/0018840 A1 | 1/2014 | Morgan et al. |
| 2014/0025041 A1 | 1/2014 | Fukuoka et al. |
| 2014/0128659 A1 | 5/2014 | Heuring et al. |
| 2014/0275722 A1 | 9/2014 | Zimmermann et al. |
| 2014/0350658 A1* | 11/2014 | Benary .................. A61F 2/856 623/1.15 |
| 2015/0018597 A1 | 1/2015 | Fierens et al. |
| 2015/0119633 A1 | 4/2015 | Haselby et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0136343 A1 | 5/2016 | Anagnostopoulos |
| 2016/0279310 A1 | 9/2016 | Scheckel et al. |
| 2017/0071769 A1 | 3/2017 | Mangiardi |
| 2017/0100527 A1 | 4/2017 | Schwammenthal et al. |
| 2018/0126130 A1 | 5/2018 | Nitzan et al. |
| 2018/0149165 A1 | 5/2018 | Siess et al. |
| 2018/0303993 A1 | 10/2018 | Schwammenthal et al. |

(56) References Cited

U.S. PATENT DOCUMENTS

FOREIGN PATENT DOCUMENTS

| | | |
|---|---|---|
| EP | 3108909 A1 | 12/2016 |
| JP | 2012505038 A | 3/2012 |
| WO | 90/13321 | 11/1990 |
| WO | 1994/01148 A1 | 1/1994 |
| WO | 9744071 A1 | 11/1997 |
| WO | 99/34847 | 7/1999 |
| WO | 2001/083016 A2 | 5/2000 |
| WO | 2002/070039 A2 | 3/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007127477 A2 | 11/2007 |
| WO | 2008005747 A2 | 1/2008 |
| WO | 2008055301 A1 | 5/2008 |
| WO | 2009010963 A2 | 1/2009 |
| WO | 2009091965 A1 | 7/2009 |
| WO | 2009129481 A1 | 10/2009 |
| WO | 2010150208 A2 | 12/2010 |
| WO | 2011035926 A1 | 3/2011 |
| WO | 2011076441 A1 | 6/2011 |
| WO | 2012007141 A1 | 1/2012 |
| WO | 2013032849 A1 | 3/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015177793 A2 | 11/2015 |
| WO | 2016185473 A1 | 11/2016 |
| WO | 2018061001 A2 | 4/2018 |
| WO | 2018061002 A1 | 4/2018 |
| WO | 2018220589 A1 | 12/2018 |

OTHER PUBLICATIONS

Corrected Notice of Allowance for U.S. Appl. No. 15/423,368 dated Apr. 17, 2019.
Final Office Action for U.S. Appl. No. 15/312,034 dated Jan. 17, 2019.
International Search Report and Written Opinion from International Application No. PCT/IL2017/051273 dated Apr. 17, 2018.
International Search Report and Written Opinion from International Application No. PCT/IL2019/050334 dated Jun. 17, 2019.
Issue Notification for U.S. Appl. No. 15/423,368 dated May 8, 2019.
Issue Notification for U.S. Appl. No. 16/022,445 dated Jul. 10, 2019.
Notice of Allowance for U.S. Appl. No. 15/312,034 dated Jun. 27, 2019.
Notice of Allowance for U.S. Appl. No. 15/423,368 dated Apr. 4, 2019.
Notice of Allowance for U.S. Appl. No. 15/423,368 dated Nov. 13, 2018.
Notice of Allowance for U.S. Appl. No. 16/022,445 dated Mar. 18, 2019.
Office Action for Australian Application No. 2015262870 dated Apr. 29, 2019.
Office Action for Australian Application No. 2019202647 dated Jun. 26, 2019.
Office Action for Japanese Application No. 2015/562562 dated Jan. 29, 2019.
Office Action for Japanese Application No. 2016/568548 dated Mar. 18, 2019.
Restriction Requirement for U.S. Appl. No. 15/888,771 dated Apr. 15, 2019.
U.S. Appl. No. 14/405,144, filed Dec. 2, 2014.
U.S. Appl. No. 15/423,368, filed Feb. 2, 2017.
U.S. Appl. No. 16/273,898, filed Feb. 12, 2019.
U.S. Appl. No. 16/345,389, filed Apr. 26, 2019.
U.S. Appl. No. 62/425,814, filed Nov. 23, 2016.
Corrected Notice of Allowance for U.S. Appl. No. 15/312,034 dated Feb. 12, 2020.
Issue Notification for U.S. Appl. No. 15/312,034 dated Feb. 19, 2020.
Non-Final Office Action for U.S. Appl. No. 15/574,948 dated Jan. 13, 2020.
Non-Final Office Action for U.S. Appl. No. 15/888,771 dated Oct. 4, 2019.
Non-Final Office Action for U.S. Appl. No. 16/035,871 dated Jan. 22, 2020.
Notice of Allowance for U.S. Appl. No. 15/312,034 dated Jan. 15, 2020.
Office Action for Chinese Application No. 201810418034.0 and dated Nov. 1, 2019.
Restriction Requirement for U.S. Appl. No. 16/035,871, dated Sep. 27, 2019.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/281,264, filed Feb. 21, 2019.
U.S. Appl. No. 16/677,893, filed Nov. 8, 2019.
U.S. Appl. No. 16/682,016, filed Nov. 13, 2019.
Extended European Search Report for EP Patent Application No. 19212211.7 dated Mar. 31, 2020.
Extended European Search Report for EP Patent Application No. 19215724.6 dated Apr. 1, 2020.
Extended European Search Report for EP Patent Application No. 19216488.7 dated Apr. 1, 2020.
Extended European Search Report for EP Patent Application No. 19216593.4 dated Apr. 6, 2020.
Final Office Action for U.S. Appl. No. 15/574,948 dated Aug. 26, 2020.
Final Office Action for U.S. Appl. No. 15/888,771 dated Apr. 28,.
Non-Final Office Action for U.S. Appl. No. 16/273,898 dated Jun. 18, 2020.
Non-Final Office Action for U.S. Appl. No. 16/278,323 dated May 22, 2020.
U.S. Appl. No. 15/574,948, filed Nov. 17, 2017.
U.S. Appl. No. 16/859,100, filed Apr. 27, 2020.
U.S. Appl. No. 16/859,492, filed Apr. 27, 2020.
European Search Report for European Application No. 13800935 dated Jan. 12, 2016.
European Search Report for European Application No. 14762232.8 dated Sep. 28, 2016.
Final Office Action for U.S. Appl. No. 14/931,363 dated Jun. 1, 2017.
International Search Report and Written Opinion for International Application No. PCT/IL2015/050532 dated Jan. 27, 2016.
International Search Report and Written Opinion for International Application No. PCT/IL2016/050525 dated Oct. 14, 2016.
International Search Report and Written Opinion for International Application No. PCT/IL2013/050495 dated Nov. 22, 2013.
International Search Report and Written Opinion for International Application No. PCT/IL2014/050289 dated Sep. 11, 2014.
International Search Report and Written Opinion from International Application No. PCT/IL2017/051092 dated Jan. 16, 2018.
Invitation to pay additional fees for International Application No. PCT/IL2015/050532 dated Nov. 17, 2015.
Issue Notification for U.S. Appl. No. 14/931,363 dated Feb. 21, 2018.
Japanese Office Action for Japanese Patent Application No. 2015-562562 dated Jun. 13, 2018.
Japanese Office Action for Japanese Patent Application No. 2015562562 dated Oct. 27, 2017.
Non-Final Office Action for U.S. Appl. No. 14/405,144 dated Feb. 22, 2016.
Non-Final Office Action for U.S. Appl. No. 14/405,144 dated Jul. 14, 2016.
Non-Final Office Action for U.S. Appl. No. 14/567,439 dated Nov. 16, 2016.
Non-Final Office Action for U.S. Appl. No. 14/774,081 dated May 24, 2017.

(56) References Cited

OTHER PUBLICATIONS

Non-Final Office Action for U.S. Appl. No. 14/774,081 dated Oct. 12, 2017.
Non-Final Office Action for U.S. Appl. No. 14/931,363 dated Feb. 15, 2017.
Non-Final Office Action for U.S. Appl. No. 14/931,363 dated Oct. 3, 2016.
Non-Final Office Action for U.S. Appl. No. 15/423,368 dated Jun. 6, 2018.
Non-Final Office Action for U.S. Appl. No. 16/022,445 dated Aug. 9, 2018.
Notice of Allowance for U.S. Appl. No. 14/567,439 dated Jun. 2, 2017.
Notice of Allowance for U.S. Appl. No. 14/774,081 dated Apr. 11, 2018.
Notice of Allowance for U.S. Appl. No. 14/931,363 dated Dec. 12, 2017.
Notice of Allowance for U.S. Appl. No. 14/931,363 dated Oct. 12, 2017.
Office Action for Chinese Application No. 201380037335.4 dated Oct. 17, 2016.
Office Action for Chinese Patent Application No. 201380037335.4 dated Mar. 22, 2017.
Office Action for Chinese Patent Application No. 201380037335.4 dated Sep. 20, 2017.
Office Action for European Application No. 13800935 dated Sep. 30, 2016.
Restriction Requirement for U.S. Appl. No. 14/567,439 dated Aug. 23, 2016.
Restriction Requirement for U.S. Appl. No. 14/774,081 dated Mar. 9, 2017.
Restriction Requirement for U.S. Appl. No. 14/931,363 dated Jul. 22, 2016.
U.S. Appl. No. 14/567,439, filed Dec. 11, 2014.
U.S. Appl. No. 14/774,081, filed Sep. 9, 2015.
U.S. Appl. No. 16/022,445, filed Jun. 28, 2018.
U.S. Appl. No. 16/278,323, filed Feb. 18, 2019.
U.S. Appl. No. 16/281,385, filed Feb. 21, 2019.
U.S. Appl. No. 61/656,244, filed Jun. 6, 2013.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403 dated Sep. 29, 2016.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart", Expert review of cardiovascular therapy, 7.9, 2009, pp. 1067-1077.
Burnett, et al., "Renal Interstitial Pressure and Sodium Excretion During Renal Vein Constriction", American Physiological Society, 1980, pp. F279-F282.
Coxworth, , "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, vol. 9, 2007, pp. 872-878.
Damman, et al., "Increased Central Venous Pressure is Associated With Impaired Renal Function and Mortality in a Broad Spectrum of Patients With Cardiovascular Disease", Journal of American College of Cardiology, vol. 53, 2009, pp. 582-588.
Doty, et al., "The Effect of Increased Renal Venous Pressure on Renal Function", The Journal of Trauma vol. 47(6), Dec. 1999, pp. 1000-1003.
Felker, et al., "Anemia as a Risk Factor and Therapeutic Target in Heart Failure", Journal of the American College of Cardiology, vol. 44, 2004, pp. 959-966.
Firth, et al., "Raised Venous Pressure: A Direct Cause of Sodium Retention in Oedema?", The Lancet, May 7, 1988, pp. 1033-1036.
Forman, et al., "Incidence, Predictors at Admission, and Impact of Worsening Renal Function Among Patients Hospitalized With Heart Failure", Journal of American College of Cardiology, vol. 43, 2004, pp. 61-67.
Fraser, et al., "The use of computational fluid dynamics in the development of ventricular assist devices", Medical engineering & physics, 33.3, 2011, pp. 263-280.
Gomes, et al., "Heterologous valve implantation in the infra-renal vena cava for treatment of the iliac venous valve regurgitation disease", experimental study; Rev Bras Cir Cardiovasc, 17(4), 2002, pp. 367-369.
Haddy, et al., "Effect of Elevation of Intraluminal Pressure on Renal Vascular Resistance", Circulation Research Journal of the American Heart Association, vol. 4, 1956, pp. 659-663.
Heywood, et al., "High prevalence of renal dysfunction and its impact on outcome in 118,465 patients hospitalized with acute decompensated heart failure", a report from the ADHERE database. J Cardiac Fail, vol. 13, 2007, pp. 422-430.
Hillege, et al., "Renal Function as a Predictor of Outcome in a Broad Spectrum of Patients With Heart Failure", Circulation Journal of the American Heart Association, vol. 113, 2006, pp. 671-678.
Hillege, et al., "Renal Function, Neurohormonal Activation, and Survival in Patients With Chronic Heart Failure", Circulation Journal of the American Heart Association, vol. 102, 2000, pp. 203-210.
Hsu, et al., "Review of recent patents on foldable ventricular assist devices", Recent Patents on Biomedical Engineering, 5.3, 2012, pp. 208-222.
Ikari, , "The Physics of Guiding Catheter; The Ikari Guiding Catheter in TRI", available at httu:i /www.docstoc.com/docs/148136553/The-[KARI-catheter---anovel-guide-for-TRI--, uploaded on Mar. 8, 2013.
Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Lauten, et al., "Heterotopic Transcatheter Tricuspid Valve Implantation: First-In-Man Application of a Novel Approach to Tricuspid Regurgitation", European Heart Journal, (1-7 as printed), Feb. 15, 2011, pp. 1207-1213.
Mcalister, et al., "Renal Insufficiency and Heart Failure: Prognostic and Therapeutic Implications From a Prospective Cohort Study", Circulation Journal of the American Heart Association, 109, 2004, pp. 1004-1009.
Mullens, et al., "Elevated Intra-Abdominal Pressure in Acute Decompensated Heart Failure. A Potential Contributor to Worsening Renal Function", Journal of the American College of Cardiology, vol. 51, 2008, pp. 300-306.
Mullens, et al., "Importance of Venous Congestion for Worsening of Renal Function in Advanced Decompensated Heart Failure", Journal of American College of Cardiology, vol. 53, 2009, pp. 589-596.
Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, vol. 14, 2008, pp. 508-514.
Notarius, et al., "Central Venous Pressure During Exercise: Role of Muscle Pump", Canadian Journal of Physiology and Pharmacology, vol. 74(6), 1996, pp. 647-651.
Park, et al., "Nutcracker Syndrome: Intravascular Stenting Approach", Nephrol Dial Transplant, vol. 15, 2000, pp. 99-101.
Reul, et al., "Blood pumps for circulatory support", Perfusion-Sevenoaks, 15.4, 2000, pp. 295-312.

(56) References Cited

OTHER PUBLICATIONS

Schmitz-Rode, et al., "An Expandable Percutaneous Catheter Pump for Left Ventricular Support", Journal of the American College of Cardiology, vol. 45, 2005, pp. 1856-1861.
Semple, et al., "Effect of Increased Renal Venous Pressure on Circulatory "Autoregulation" of Isolated Dog Kidneys", Circulation Research Journal of the American Heart Association, vol. 7, 1959, pp. 643-648.
Song, et al., "Axial flow blood pumps", ASAIO journal, 49, 2003, pp. 355-364.
Tang, et al., "Anemia in Chronic Heart Failure: Prevalence, Etiology, Clinical Correlates, and Treatment Options", Circulation Journal of the American Heart Association, vol. 113, 2006, pp. 2454-2461.
Throckmorton, et al., "Design of a protective cage for an intra vascular axial flow blood pump to mechanically assist the failing Fontan", Artificial organs, 33.8, 2009, pp. 611-621.
Thunberg, et al., "Ventricular assist devices today and tomorrow", Journal of cardiothoracic and vascular anesthesia, 24.4, 2010, pp. 656-680.
Timms, , "A review of clinical ventricular assist devices", Medical engineering & physics, 33.9, 2011, pp. 1041-1047.
Uthoff, et al., "Central venous pressure at emergency room presentation predicts cardiac rehospitalization in patients with decompensated heart failure", European Journal of Heart Failure, 12, 2010, pp. 469-476.
Wencker, , "Acute Cardio-Renal Syndrome: Progression From Congestive Heart Failure to Congestive Kidney Failure", Current Heart Failure Reports, vol. 4, 2007, pp. 134-138.
Winton, , "The Control of Glomerular Pressure by Vascular Changes Within the Mammalian Kidney, Demonstrated by the Actions of Adrenaline", Journal of Physiology, vol. 73, Nov. 1931, pp. 151-162.
Winton, , "The Influence of Venous Pressure on the Isolated Mammalian Kidney", Journal of Physiology, vol. 72(1), Jun. 6, 1931, pp. 49-61.
Wood, , "The Mechanism of the Increased Venous Pressure With Exercise in Congestive Heart Failure", Journal of Clinical Investigation, vol. 41(11), 1962, pp. 2020-2024.
Wu, et al., "Design and simulation of axial flow maglev blood pump", International Journal of Information Engineering and Electronic Business, 3.2, 2011, p. 42.
Yancy, et al., "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, vol. 47(1), 2006, pp. 76-84.
Extended European Search Report for European Application No. 20179137.3 dated Oct. 9, 2020.
Final Office Action for U.S. Appl. No. 16/273,898 dated Nov. 5, 2020.
International Search Report and Written Opinion from International Application No. PCT/162020/054759 dated Nov. 13, 2020.
Issue Notification for U.S. Appl. No. 16/035,871 dated Dec. 29, 2020.
Issue Notification for U.S. Appl. No. 16/278,323 dated Nov. 24, 2020.
Non-Final Office Action for U.S. Appl. No. 16/281,385 dated Oct. 14, 2020.
Non-Final Office Action for U.S. Appl. No. 16/345,389 dated Oct. 26, 2020.
Notice of Allowance for U.S. Appl. No. 16/035,871 dated Aug. 2020.
Notice of Allowance for U.S. Appl. No. 16/035,871 dated Dec. 4, 2020.
Notice of Allowance for U.S. Appl. No. 16/278,323 dated Oct. 2020.
Office Action for Australian Application No. 2020201055 dated Sep. 15, 2020.
Office Action for Chinese Application No. 201810418034.0 dated Aug. 4, 2020.
Office Action for Chinese Application No. 201810418034.0 dated Dec. 24, 2020.
Office Action for Chinese Application No. 201811196500.1 dated Aug. 28, 2020.

* cited by examiner

BLOOD VESSEL TUBE

CROSS-REFERENCE TO RELATED APPLICATION

The present application is a US national phase application of PCT Application No. PCT/IL/2017/051092 to Tuval (published as WO 18/061002), filed Sep. 28, 2017, which claims priority from U.S. Provisional Patent Application 62/401,403 to Tuval, filed Sep. 29, 2016, entitled "Blood vessel tube," which is incorporated herein by reference.

FIELD OF EMBODIMENTS OF THE INVENTION

Some applications of the present invention generally relate to medical apparatus. Specifically, some applications of the present invention relate to apparatus and methods associated with placing a passive medical device in a subject's vena cava.

BACKGROUND

It is common for cardiac dysfunction or congestive heart failure to develop into kidney dysfunction, which, in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neurohormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This pathophysiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: A reduction in the kidney's erythropoietin production, hemodilution by fluid retention, and an inflammatory response leading to a reduced gastro-intestinal iron uptake.

Mechanistically, increased renal venous pressure may cause intracapsular pressure and, subsequently, interstitial peritubular pressure, to rise. A rise in peritubular pressure may impact tubular function (reduce sodium excretion), as well as diminish glomerular filtration, by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration), has been shown to reduce plasma creatinine levels.

Increased venous return resulting from activation of the "leg muscle pump" during physical activity such as walking may raise systemic venous pressure, particularly in heart failure patients, and may result in reflux into the renal veins.

SUMMARY OF EMBODIMENTS

In accordance with some applications of the present invention, a subject is identified as suffering from cardiac dysfunction, congestive heart failure, reduced renal blood flow, increased renal vascular resistance, arterial hypertension, diabetes, and/or kidney dysfunction. In response thereto, a venturi tube is placed inside the subject's vena cava. The venturi tube (when disposed in a non-constrained configuration) defines a flared downstream portion that diverges toward a downstream end of the tube, and a flared upstream portion that diverges toward an upstream end of the tube, such that a central portion of the tube is narrower than at the ends of the tube. The tube defines one or more lateral openings along the central portion of the tube. The tube is placed within the subject's vena cava, such that the downstream portion of the tube is sealed with respect to the inner wall of the vena cava at a location that is downstream of junctions of the vena cava with all of the subject's renal veins, and the upstream portion of the tube is sealed with respect to the inner wall of the vena cava at a location that is upstream of junctions of the vena cava with all of the subject's renal veins.

The tube, when placed in the vena cava in the above-described manner, is configured to cause blood flow through the tube to undergo the venturi effect as it passes through the tube. That is, the tube generates a region of low pressure between the ends of the tube, due to the blood flowing from the upstream end of the tube through the narrow central region of the tube. Pressure within the central region of the tube is lower than the pressure in the subject's renal veins in the absence of the tube. Therefore, blood from the subject's renal veins is drawn into the tube, via the lateral opening defined by the tube. In this manner, pressure within the subject's renal veins is reduced.

For some applications, a generally similar effect to that described above with reference to the placement of a venturi tube in the vena cava is achieved by placing a first nozzle in the subject's vena cava upstream of junctions of the vena cava with all of the subject's renal veins, such that the first nozzle converges in a direction of antegrade blood flow through the vena cava, and placing a second nozzle in the subject's vena cava downstream of the junctions of the vena cava with all of the subject's renal veins. Due the convergence of the first nozzle, blood flowing through the nozzle undergoes the venturi effect, thereby creating a region within the vena cava downstream of the nozzle that has a lower blood pressure than the blood pressure in the renal veins in the absence of the nozzle. Therefore, blood from the subject's renal veins is drawn into the region within the vena cava that is downstream of the nozzle. In this manner, pressure within the subject's renal veins is reduced.

For some applications, the second nozzle is placed in the subject's vena cava, such that the second nozzle converges in the direction of antegrade blood flow through the vena cava. The second nozzle is configured to impede backflow of blood toward the low-pressure region from regions within the vena cava that are downstream of the junctions of the vena cava with the subject's renal veins. Alternatively, the second nozzle is placed in the subject's vena cava, such that the second nozzle diverges in the direction of antegrade blood flow through the vena cava (i.e., the second nozzle converges in the direction of retrograde blood flow through the vena cava). The second nozzle is configured to impede backflow of blood toward the low-pressure region from regions within the vena cava that are downstream of the junctions of the vena cava with the subject's renal veins. Furthermore, the second nozzle is configured to cause any blood that does flow back, via the second nozzle toward the low-pressure region, to undergo the venturi effect by virtue of having flowed through the nozzle. Therefore, backflowing blood that passes through the nozzle is caused to be at low pressure once it passes through the nozzle.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

There is therefore provided, in accordance with some applications of the present invention, apparatus for use with renal veins and a vena cava of a subject, the apparatus including:
  a tube that defines:
    a flared downstream portion thereof that diverges toward a downstream end of the tube, and a flared upstream portion thereof that diverges toward an upstream end of the tube, such that a central portion of the tube is narrower than at the ends of the tube, and
    a plurality of lateral openings; and
  a support frame configured to support the tube within the subject's vena cava, such that:
    the downstream portion of the tube is sealed with respect to an inner wall of the vena cava at a location that is downstream of junctions of the vena cava with all of the subject's renal veins, and
    the upstream portion of the tube is sealed with respect to the inner wall of the vena cava at a location that is upstream of junctions of the vena cava with all of the subject's renal veins.

In some applications, the plurality of lateral openings are shaped such as to converge toward a longitudinal axis of the tube.

In some applications, an inner diameter of the tube at a location at which the inner diameter is at its maximum is greater than 12 mm.

In some applications, an inner diameter of the tube at a location at which the inner diameter is at its minimum is less than 8 mm.

In some applications, a ratio between an inner diameter of the tube at a location at which the inner diameter is at its maximum and an inner diameter of the tube at a location at which the inner diameter is at its minimum is greater than 3:1.

In some applications, a length of the tube is greater than 20 mm.

In some applications, the apparatus further includes:
  one or more blood pressure sensors configured to measure blood pressure within the vena cava; and
  a computer processor configured to modulate a diameter of the central portion of the tube responsively to the measured blood pressure.

In some applications, the one or more blood pressure sensors are configured to measure an indication of renal venous pressure of the subject.

In some applications, the one or more blood pressure sensors are configured to measure an indication of central venous pressure of the subject.

In some applications, the one or more blood pressure sensors are configured to measure an indication of lower-body venous pressure of the subject.

There is further provided, in accordance with some applications of the present invention, a method for use with renal veins and a vena cava of a subject, the method including:
  providing a tube that defines:
    a flared downstream portion thereof that diverges toward a downstream end of the tube, and a flared upstream portion thereof that diverges toward an upstream end of the tube, such that a central portion of the tube is narrower than at the ends of the tube, and
    a plurality of lateral openings; and
  placing the tube within the subject's vena cava, such that:
    the downstream portion of the tube is sealed with respect to an inner wall of the vena cava at a location that is downstream of junctions of the vena cava with all of the subject's renal veins, and
    the upstream portion of the tube is sealed with respect to the inner wall of the vena cava at a location that is upstream of junctions of the vena cava with all of the subject's renal veins.

In some applications, providing the tube includes providing the tube, the plurality of lateral openings being shaped such as to converge toward a longitudinal axis of the tube.

In some applications, providing the tube includes providing the tube, an inner diameter of the tube at a location at which the inner diameter is at its maximum being greater than 12 mm.

In some applications, providing the tube includes providing the tube, an inner diameter of the tube at a location at which the inner diameter is at its minimum being less than 8 mm.

In some applications, providing the tube includes providing the tube, a ratio between an inner diameter of the tube at a location at which the inner diameter is at its maximum and an inner diameter of the tube at a location at which the inner diameter is at its minimum being greater than 3:1.

In some applications, providing the tube includes providing the tube, a length of the tube being greater than 20 mm.

In some applications, the method further includes:
  measuring blood pressure within the vena cava; and
  modulating a diameter of the central portion of the tube responsively to the measured blood pressure.

In some applications, measuring blood pressure within the vena cava includes measuring an indication of renal venous pressure of the subject.

In some applications, measuring blood pressure within the vena cava includes measuring an indication of central venous pressure of the subject.

In some applications, measuring blood pressure within the vena cava includes measuring an indication of lower-body venous pressure of the subject.

In some applications, the method further includes identifying the subject as suffering from a condition selected from the group consisting of: cardiac dysfunction, congestive heart failure, reduced renal blood flow, increased renal vascular resistance, arterial hypertension, diabetes, and kidney dysfunction, and placing the tube within the subject's vena cava includes placing the tube within the subject's vena cava, in response to identifying the subject as suffering from the selected condition.

In some applications, placing the tube within the subject's vena cava includes treating the selected condition by reducing renal venous pressure of the subject.

There is further provided, in accordance with some applications of the present invention, a method for use with renal veins and a vena cava of a subject, the method including:

placing a first nozzle in the subject's vena cava upstream of junctions of the vena cava with all of the subject's renal veins, such that the first nozzle converges in a direction of antegrade blood flow through the vena cava; and placing a second nozzle in the subject's vena cava downstream of the junctions of the vena cava with all of the subject's renal veins.

In some applications, placing the second nozzle in the subject's vena cava includes placing the second nozzle in the subject's vena cava, such that the second nozzle converges in the direction of antegrade blood flow through the vena cava.

In some applications, placing the second nozzle in the subject's vena cava includes placing the second nozzle in the subject's vena cava, such that the second nozzle diverges in the direction of antegrade blood flow through the vena cava.

In some applications, the method further includes:
measuring blood pressure within the vena cava; and
modulating a diameter of an opening defined by the first nozzle responsively to the measured blood pressure.

In some applications, measuring blood pressure within the vena cava includes measuring an indication of renal venous pressure of the subject.

In some applications, measuring blood pressure within the vena cava includes measuring an indication of central venous pressure of the subject.

In some applications, measuring blood pressure within the vena cava includes measuring an indication of lower-body venous pressure of the subject.

In some applications, the method further includes modulating a diameter of an opening defined by the second nozzle responsively to the measured blood pressure.

In some applications, the method further includes:
measuring blood pressure within the vena cava; and
modulating a diameter of an opening defined by the second nozzle responsively to the measured blood pressure.

In some applications, measuring blood pressure within the vena cava includes measuring an indication of renal venous pressure of the subject.

In some applications, measuring blood pressure within the vena cava includes measuring an indication of central venous pressure of the subject.

In some applications, measuring blood pressure within the vena cava includes measuring an indication of lower-body venous pressure of the subject.

In some applications, the method further includes identifying the subject as suffering from a condition selected from the group consisting of: cardiac dysfunction, congestive heart failure, reduced renal blood flow, increased renal vascular resistance, arterial hypertension, diabetes, and kidney dysfunction, and placing the first and second nozzles in the subject's vena cava includes placing the first and second nozzles in the subject's vena cava, in response to identifying the subject as suffering from the selected condition.

In some applications, placing the first and second nozzles in the subject's vena cava includes treating the selected condition by reducing renal venous pressure of the subject.

There is further provided, in accordance with some applications of the present invention, apparatus for use with renal veins and a vena cava of a subject, the apparatus including:

a first nozzle configured to be placed in the subject's vena cava upstream of junctions of the vena cava with all of the subject's renal veins, such that the first nozzle converges in a direction of antegrade blood flow through the vena cava; and a second nozzle in the subject's vena cava downstream of the junctions of the vena cava with all of the subject's renal veins.

In some applications, the second nozzle is configured to be placed in the subject's vena cava, such that the second nozzle converges in the direction of antegrade blood flow through the vena cava.

In some applications, the second nozzle is configured to be placed in the subject's vena cava, such that the second nozzle diverges in the direction of antegrade blood flow through the vena cava.

In some applications, the apparatus further includes:
one or more blood pressure sensors configured to measure blood pressure within the vena cava; and
a computer processor configured to modulate a diameter of an opening defined by the first nozzle responsively to the measured blood pressure.

In some applications, the one or more blood pressure sensors are configured to measure an indication of renal venous pressure of the subject.

In some applications, the one or more blood pressure sensors are configured to measure an indication of central venous pressure of the subject.

In some applications, the one or more blood pressure sensors are configured to measure an indication of lower-body venous pressure of the subject.

In some applications, the computer processor is further configured to modulate a diameter of an opening defined by the second nozzle responsively to the measured blood pressure.

In some applications, the apparatus further includes:
one or more blood pressure sensors configured to measure blood pressure within the vena cava; and
a computer processor configured to modulate a diameter of an opening defined by the second nozzle responsively to the measured blood pressure.

In some applications, the one or more blood pressure sensors are configured to measure an indication of renal venous pressure of the subject.

In some applications, the one or more blood pressure sensors are configured to measure an indication of central venous pressure of the subject.

In some applications, the one or more blood pressure sensors are configured to measure an indication of lower-body venous pressure of the subject.

The present invention will be more fully understood from the following detailed description of embodiments thereof, taken together with the drawings, in which:

DETAILED DESCRIPTION OF EMBODIMENTS

Figure 1:
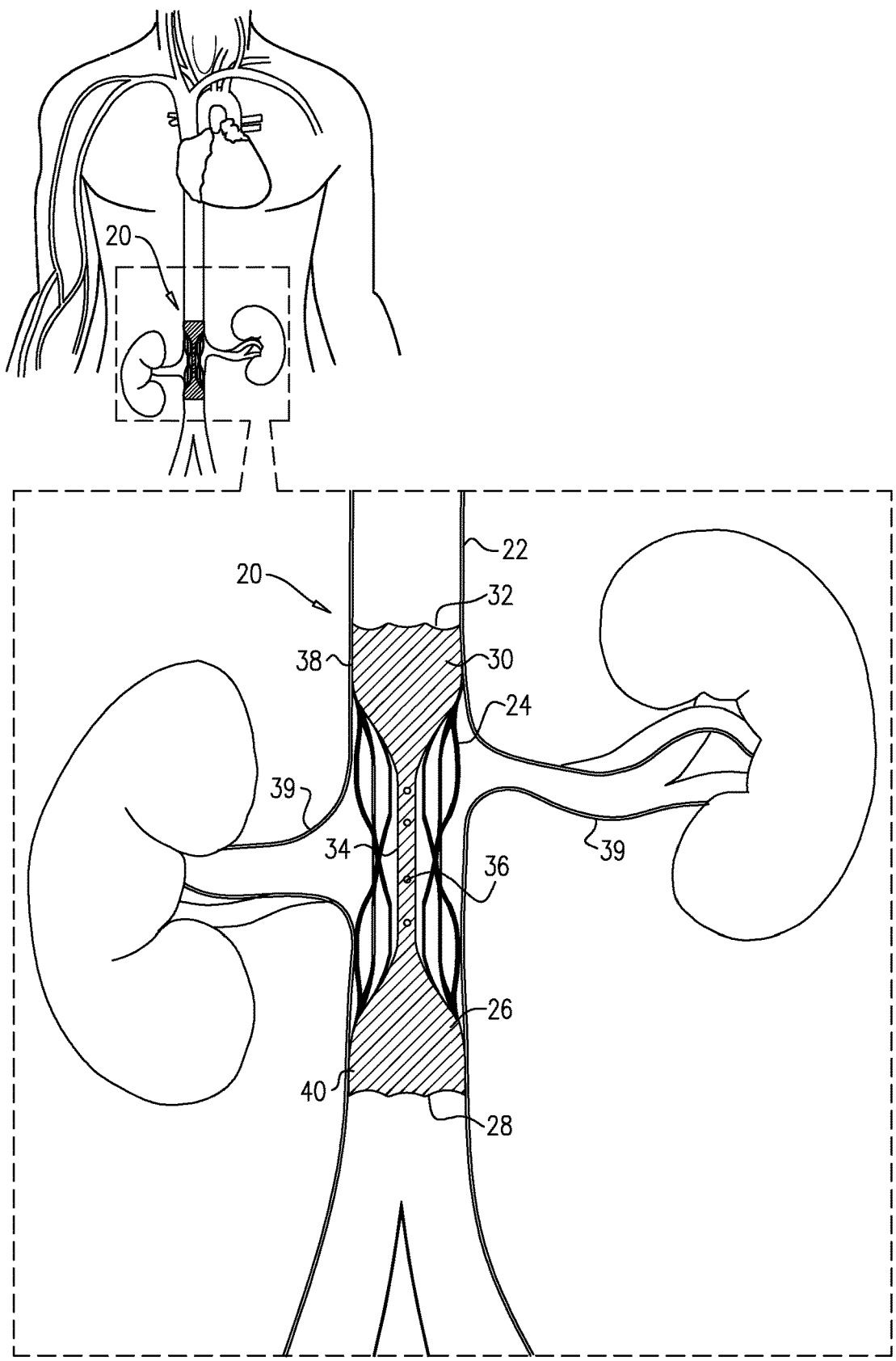
FIG. 1 is a schematic illustration of a venturi tube disposed inside a subject's vena cava, in accordance with some applications of the present invention.
Figure 2:
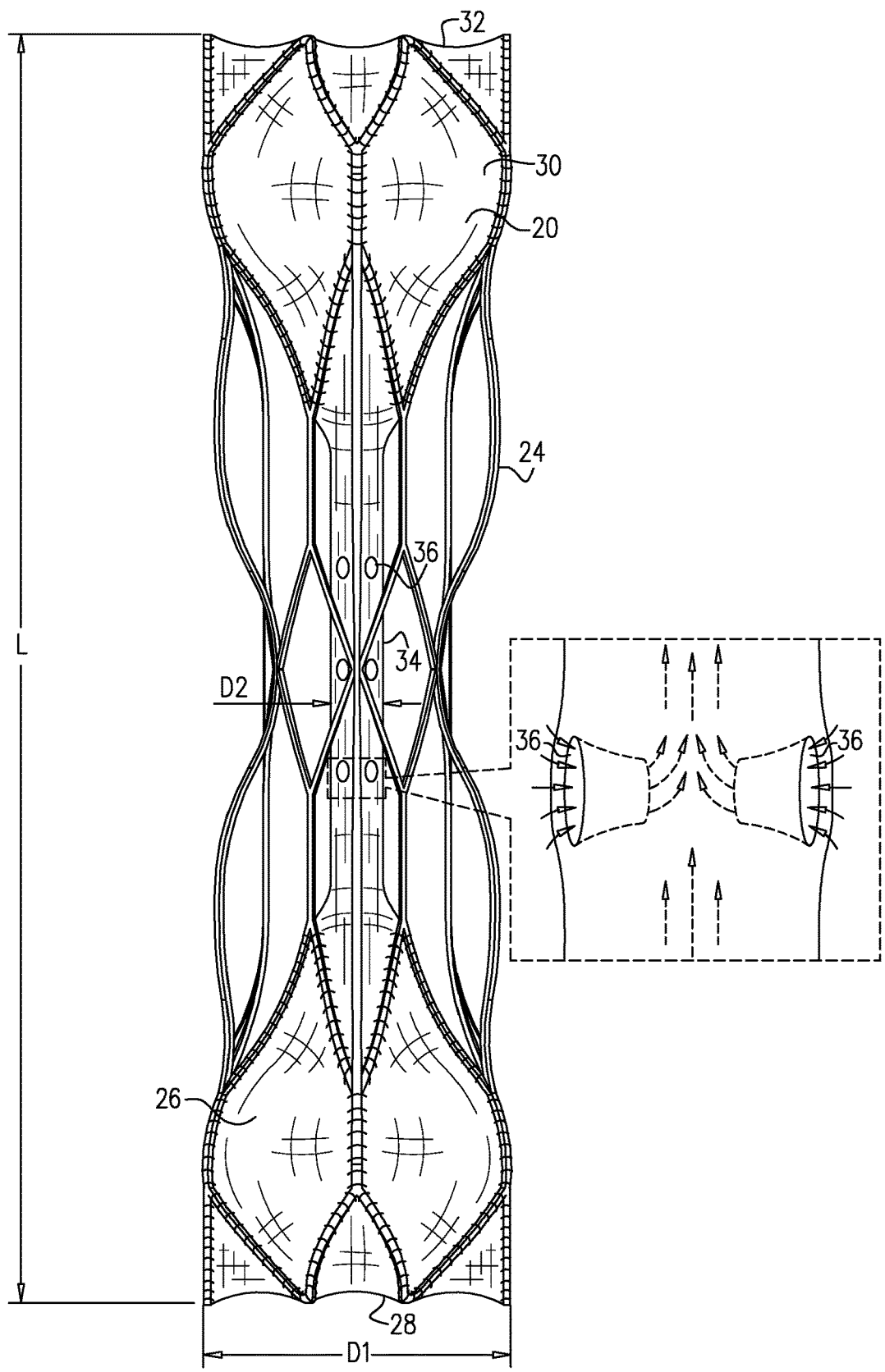
FIG. 2 is a schematic illustration of the venturi tube and a support frame for supporting the venturi tube inside the vena cava, in accordance with some applications of the present invention.

Reference is now made to FIG. 1, which is a schematic illustration of a venturi tube 20 disposed inside a subject's vena cava 22, in accordance with some applications of the present invention. Reference is also made to FIG. 2, which is a schematic illustration of venturi tube 20 and a support frame 24 for supporting the venturi tube inside the vena cava, in accordance with some applications of the present invention.

Venturi tube 20 is typically placed inside the subject's vena cava in order to provide chronic treatment for a subject suffering from cardiac dysfunction, congestive heart failure, low renal blood flow, high renal vascular resistance, arterial hypertension, diabetes, and/or kidney dysfunction. Typically, venturi tube 20 and support frame 24 are inserted into the subject's vena cava via a delivery device, such as a catheter (not shown). For example, the catheter may be advanced to the subject's vena cava via any one of the subject's femoral vein, subclavian vein, or jugular vein.

For some applications, the support frame is made of a shape-memory alloy, such as nitinol. The venturi tube is typically made of a blood-impermeable material (e.g., polyester, polyurethane, and/or a different polymer), and is coupled to the support frame (for example, via stitching, or via an adhesive). The support frame and the venturi tube are inserted into the vena cava, while in constrained configurations inside the delivery device. Upon being released from the delivery device, inside the vena cava, the support frame and the venturi tube assume their non-constrained configurations by virtue of the support frame having been shape set to its non-constrained configuration. The support frame and the venturi tube are shown in their non-constrained configurations in FIGS. 1 and 2.

Venturi tube 20 (when disposed in its non-constrained configuration) defines a flared upstream portion 26 that diverges toward an upstream end 28 of the tube, and a flared downstream portion 30 that diverges toward a downstream end 32 of the tube, such that a central portion 34 of the tube is narrower than at the ends of the tube. The tube defines a plurality of lateral openings 36. The tube is placed within the subject's vena cava, such that the downstream portion of the tube is sealed with respect to the inner wall of the vena cava at a location 38 that is downstream of junctions of the vena cava with all of the subject's renal veins 39, and the upstream portion is sealed with respect to the inner wall of the vena cava at a location 40 that is upstream of junctions of the vena cava with all of the subject's renal veins. Typically, the flared upstream and downstream portions of the tube become sealed with respect to the inner wall of the vena cava, by virtue of the flared portions of the tube being coupled (e.g., stitched, or bonded with adhesive) to the support frame, and the support frame radially expanding such that the support frame contacts the inner wall of the vena cava.

The tube, when placed in the vena cava in the above-described manner, is configured to cause blood flow through the tube to undergo the venturi effect as it passes through the tube. That is, the tube generates a region of low pressure between the ends of the tube, due to the blood flowing through narrow central portion 34 of the tube. Pressure within the central portion of the tube is lower than the pressure in the subject's renal veins in the absence of the tube. Therefore, blood from the subject's renal veins is drawn into the tube, via the one or more lateral openings 36 defined by the tube. In this manner, pressure within the subject's renal veins is reduced.

Typically, the reduced pressure within the central portion of the tube causes pressure within the region of the vena cava that surrounds the tube to be reduced. For some applications, due to the reduced pressure within the region of the vena cava that surrounds the tube, in the absence of support frame 24, the walls of the vena cava would collapse inwardly around against the tube. Typically, the support frame holds open the walls of the vena cava in the region surrounding the tube, such that the walls of the vena cava do not collapse inwardly as a result of the reduced pressure in the region of the vena cava surrounding the tube.

For some applications, the one or more lateral openings 36 are shaped to converge toward the longitudinal axis of the tube, as shown in the enlarged portion of FIG. 2. By being shaped in this shape, the lateral openings are configured to direct blood to flow into the interior of the tube from outside the tube.

With reference to FIG. 2, typically, (in its non-constrained configuration) inner diameter D1 of the tube at the location at which the inner diameter is at its maximum (which is typically toward the ends of the tube) is greater than 12 mm (e.g., greater than 18 mm) and/or less than 40 mm (e.g., less than 28 mm), e.g., 12-40 mm, or 18-28 mm. It is noted that, for some applications (not shown), there is a slight convergence of the tube at the ends of the tube, such that the inner diameter of the tube is at its maximum at locations that are slightly inset from the ends of the tube. Typically, (in its non-constrained configuration) inner diameter D2 of the tube at the location at which the inner diameter is at its minimum (which is typically toward the longitudinal center of the tube) is greater than 3 mm (e.g., greater than 4 mm) and/or less than 8 mm (e.g., less than 6 mm), e.g., 3-8 mm, or 4-6 mm. For some applications, as shown in FIGS. 1 and 2, the tube is at its minimum diameter (D2) over a length of up to 6 cm (e.g., between 0.5 and 6 cm, or between 2 and 6 cm), such that the narrowest portion of the tube has an elongate cylindrical shape that extends over this length. Typically, the ratio of D1 to D2 is greater than 3:1, e.g., greater than 4:1. Alternatively (application not shown), the flared downstream portion (which diverges toward to the downstream end of the tube) abuts the flared upstream portion (which diverges toward the upstream end of the tube), such that the tube is at its minimum inner diameter only at a single longitudinal location, at which the diverging upstream portion abuts the diverging downstream portion.

For some applications, a total length L of tube 20 is greater than 20 mm (e.g., greater than 50 mm) and/or less than 160 mm (e.g., less than 120 mm), e.g., 20-160 mm, or 50-120 mm.

Typically, tube 20 is placed inside the vena cava of a subject suffering from cardiac dysfunction, congestive heart failure, low renal blood flow, high renal vascular resistance, arterial hypertension, diabetes, and/or kidney dysfunction. Typically, placing tube 20 in the vena cava of such a subject causes a lowering and flattening of the subject's renal vein pressure profile, even though the subject's central venous pressure is elevated, e.g., as described with reference to FIG. 4B of WO 14/141284 to Schwammenthal, which is incorporated herein by reference.

Typically, due to the reduction in pressure in the renal veins that is caused by the placing tube 20 inside the vena cava, perfusion of the subject's kidney increases. In turn, this may cause pressure in the renal veins to rise relative to the pressure in the renal veins immediately subsequent to placing tube 20 inside the vena cava, due to increased blood flow into the renal vein. Typically, even after perfusion of the kidney increases, the placement of tube 20 inside the vena cava is configured to maintain the pressure in the renal vein at a lower value than the pressure in the renal vein before the placement of tube 20 inside the vena cava.

It is noted that, for some applications, due to the reduction in pressure in the renal vein that is caused by the placement of tube 20 inside the vena cava, the subject's renal vascular resistance decreases, in accordance with physiological mechanisms that are described, for example, in an article by Haddy et al., entitled "Effect of elevation of intraluminal pressure on renal vascular resistance" (Circulation Research, 1956), which is incorporated herein by reference. It is further noted that a treatment of the subject that increases renal perfusion by increasing blood pressure in the subject's renal arteries would typically not effect the aforementioned physiological mechanisms.

Typically, when placement of tube 20 inside the vena cava is used to reduce pressure in the subject's renal veins, it is expected that there will be an improved responsiveness by the subject to administration of diuretics to the subject, due to the reduction in renal venous pressure. Therefore, for some applications, a reduced dosage of diuretics may be administered to the subject relative to a dosage of diuretics that would be administered to the subject in the absence of performing the techniques described herein. Alternatively, a regular dosage of diuretics may be administered to the subject, but the diuretics may have a greater effect on the subject, due to the reduction in renal venous pressure.

Typically, high central venous pressure leads to a high level of blood pressure within the heart, which in turn leads to the release of atrial natriuretic peptide (ANP) and B-type natriuretic peptide (BNP) by the subject, both of which act as natural diuretics. For some applications, when placement of tube 20 inside the vena cava is used to reduce pressure in the subject's renal veins, there is expected to be an improved responsiveness by the subject to the release of the natural diuretics by the subject, due to the reduction in renal venous pressure. For some applications, since the subject's central venous pressure is not lowered by placement of tube 20 inside the vena cava, it is expected that the subject will continue to release atrial natriuretic peptide (ANP) and B-type natriuretic peptide (BNP), even while the subject's renal venous pressure is reduced by the placement of tube 20 inside the vena cava. Thus, for some applications, placement of tube 20 inside the vena cava may result in the subject continuing to release atrial natriuretic peptide (ANP) and B-type natriuretic peptide (BNP), as well as resulting in the effectiveness of the aforementioned natural diuretics being greater than the effectiveness of the diuretics in the absence of the placement of tube 20 inside the vena cava.

Figure 3:
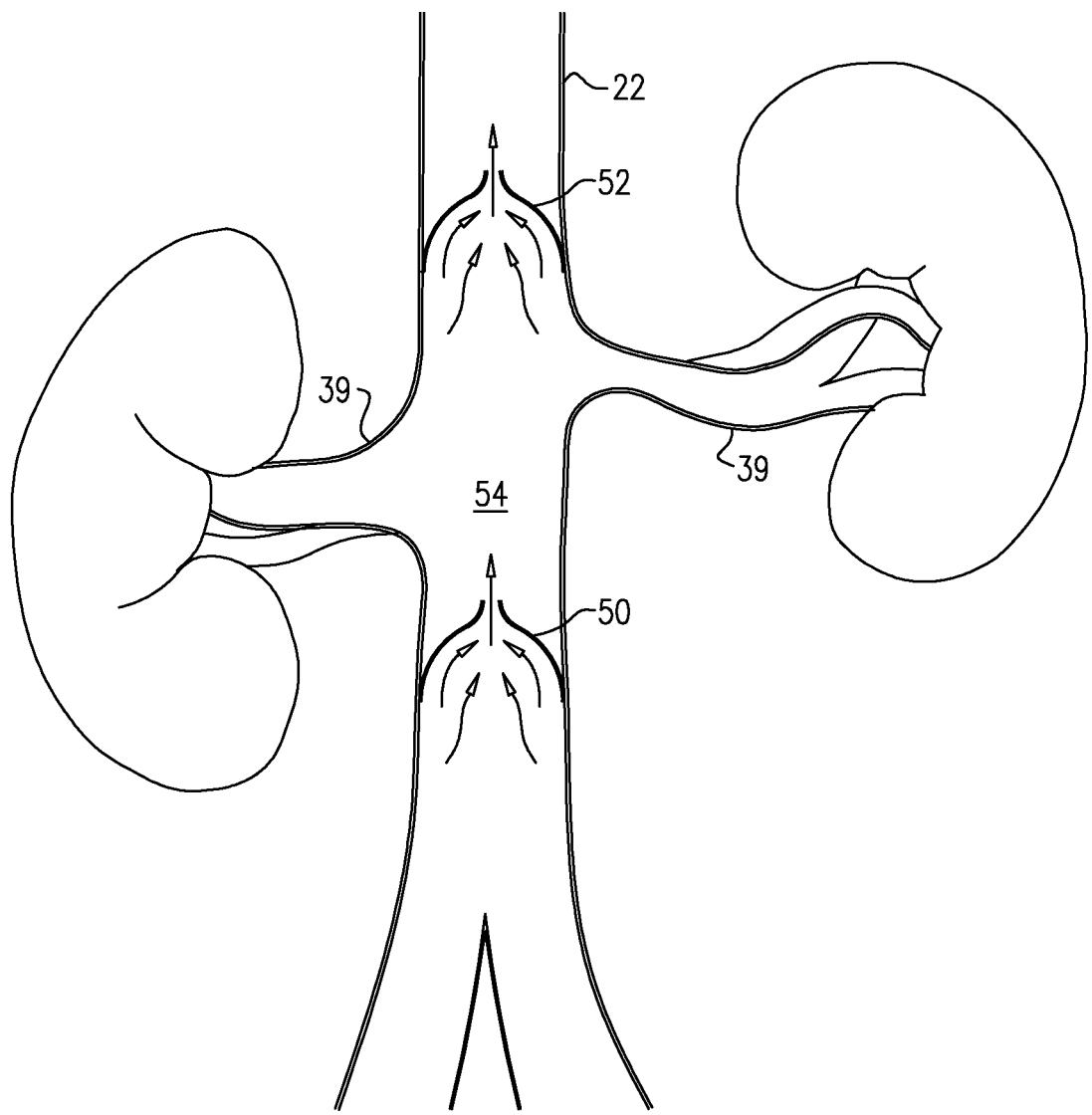
FIG. 3 is a schematic illustration of first and second nozzles disposed inside a subject's vena cava, in accordance with some applications of the present invention.
Figure 4:
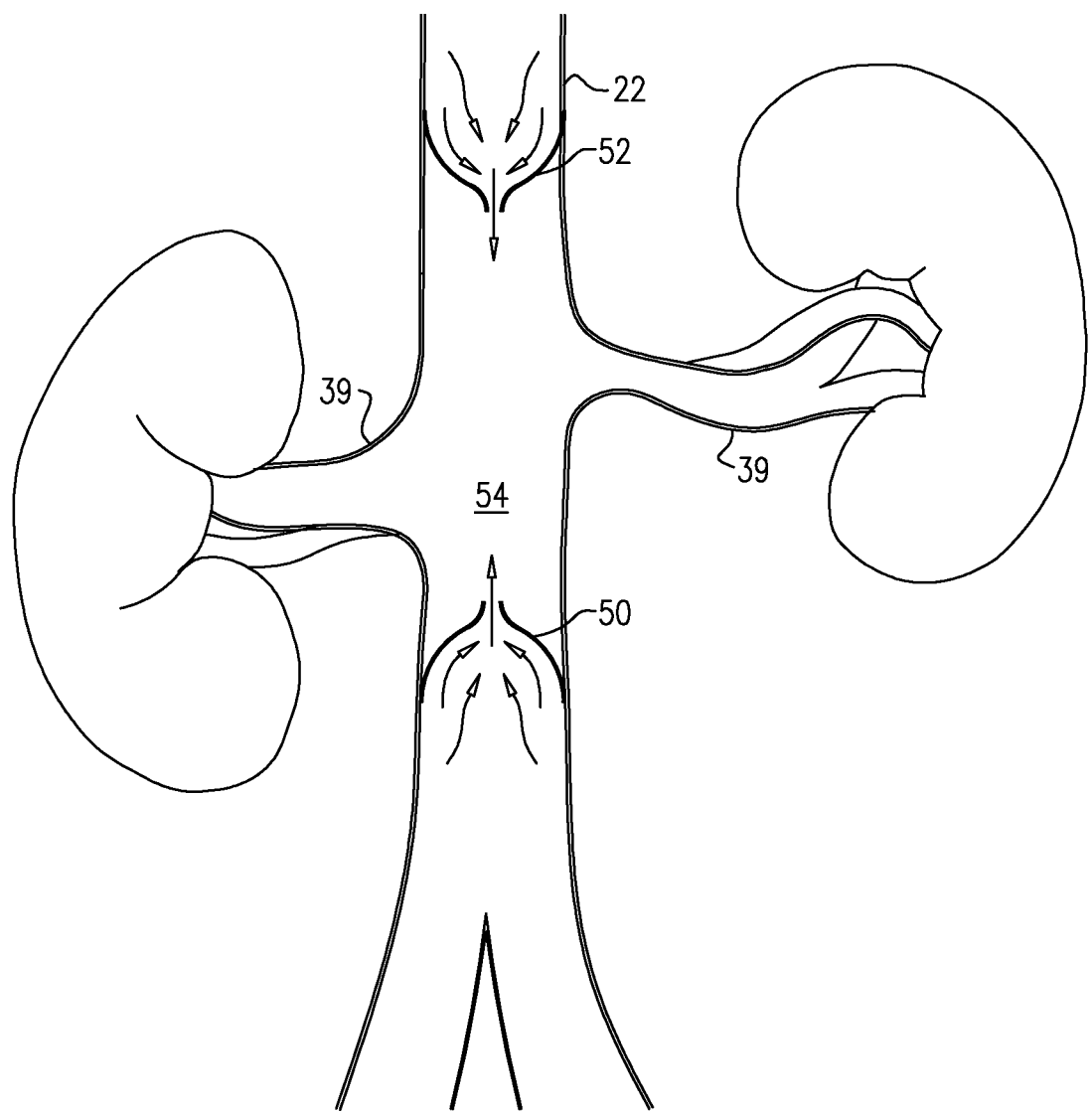
FIG. 4 is a schematic illustration of first and second nozzles disposed inside a subject's vena cava, in accordance with some applications of the present invention.

Reference is now made to FIGS. 3 and 4, which are schematic illustrations of a first nozzle 50 and a second nozzle 52 disposed inside vena cava 22, in accordance with some applications of the present invention. For some applications, a generally similar effect to that described above with reference to the placement of tube 20 in the vena cava is achieved by placing first nozzle 50 in the subject's vena cava upstream of junctions of the vena cava with all of the subject's renal veins 39, such that the first nozzle converges in a direction of antegrade blood flow through the vena cava, and placing a second nozzle 52 in the subject's vena cava downstream of the junctions of the vena cava with all of the subject's renal veins. Due the convergence of nozzle 50, blood flowing through the nozzle undergoes the venturi effect, thereby creating a region 54 within the vena cava downstream of the nozzle that has a lower blood pressure than the blood pressure in the renal veins in the absence of the nozzle. Therefore, blood from the subject's renal veins is drawn into region within the vena cava that is downstream of the nozzle. In this manner, pressure within the subject's renal veins is reduced.

For some applications, second nozzle 52 is placed in the subject's vena cava, such that the second nozzle converges in the direction of antegrade blood flow through the vena cava, as shown in FIG. 3. The second nozzle is configured to impede backflow of blood toward low pressure region 54 from regions within the vena cava that are downstream of the junctions of the vena cava with the subject's renal veins. Alternatively, the second nozzle is placed in the subject's vena cava, such that the second nozzle diverges in the direction of antegrade blood flow through the vena cava (i.e., the second nozzle converges in the direction of retrograde blood flow through the vena cava), as shown in FIG. 4. The second nozzle is configured to impede backflow of blood toward low pressure region 54 from regions within the vena cava that are downstream of the junctions of the vena cava with the subject's renal veins. Furthermore, the second nozzle is configured to cause any blood that does flow back, via the second nozzle toward the low-pressure region, to undergo the venturi effect by virtue of having flowed through the nozzle. Therefore, backflowing blood that passes through the nozzle is caused to be at low pressure once it passes through the nozzle.

Figure 5:
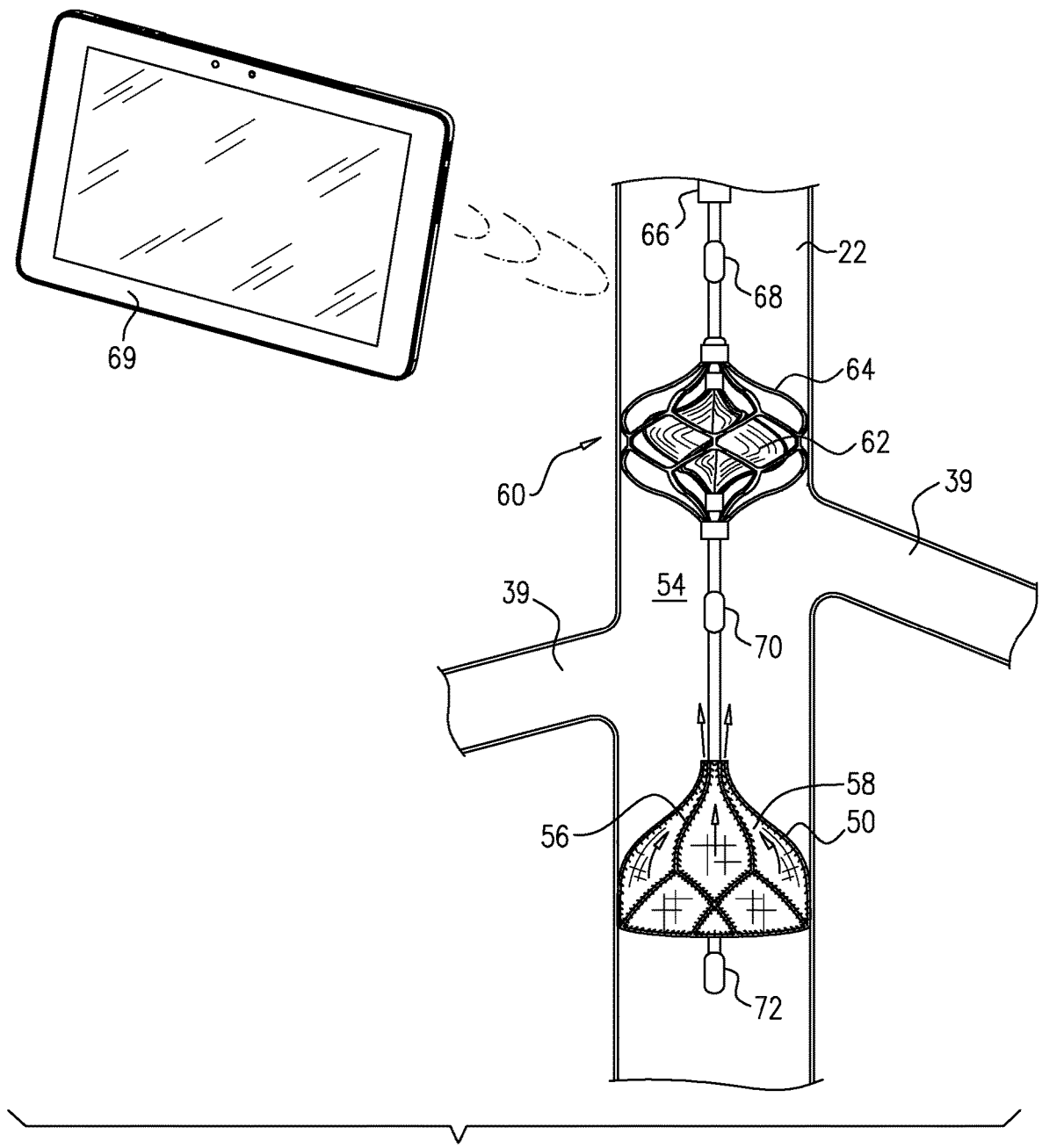
FIG. 5 is a schematic illustration of a nozzle and a pump disposed inside a subject's vena cava, in accordance with some applications of the present invention.

Reference is now made to FIG. 5, which is a schematic illustration of nozzle 50 and a blood pump 60 disposed inside a subject's vena cava, in accordance with some applications of the present invention. Nozzle 50 is generally as described hereinabove. The nozzle is placed in the subject's vena cava 22 upstream of junctions of the vena cava with all of the subject's renal veins 39, such that the nozzle converges in a direction of antegrade blood flow through the vena cava.

Blood pump 60 is placed in the subject's vena cava downstream of the junctions of the vena cava with all of the subject's renal veins and is configured to pump blood in the downstream (i.e., antegrade) direction, toward the subject's right atrium.

Typically, nozzle 50 is configured to partially occlude the subject's vena cava upstream of the junctions of the vena cava with the subject's renal veins. The nozzle is configured to partially occlude the subject's vena cava such that, in response to the pumping of the downstream blood pump, there is not a substantial increase of blood flow from the subject's lower body toward the subject heart, but such that region 54 of low pressure within the vena cava is generated, between the nozzle and the blood pump, within which the blood pressure is lower than the subject's central venous pressure. In addition, due the convergence of nozzle 50, blood flowing through the nozzle undergoes the venturi effect, thereby adding to the reduction in pressure within region 54, relative to central venous pressure. Typically, by generating a region of low pressure, blood flow from the renal veins into the vena cava increases, thereby lowering renal blood pressure and enhancing renal perfusion. It is noted that the nozzle is configured to partially occlude, but not to totally occlude, the vena cava, in such a manner as to generate a region of low pressure within the vena cava, but to allow a substantial flow of blood through the vena cava.

For some applications, blood pump 60 includes a radially-expandable impeller 62 disposed inside a radially-expandable impeller cage 64. Typically, nozzle 50 and blood pump 60 are disposed at the end of a catheter 66. The impeller and the cage of the blood pump are shape set such as to assume radially-expanded configurations thereof in the absence of any radially-constraining force acting upon the impeller and the cage. For some applications, an engagement mechanism engages the impeller and the cage with respect to one another, such that in response to the cage becoming radially constrained the impeller becomes radially constrained, e.g., in accordance with apparatus and methods described in described in WO 14/141284 to Schwammenthal, which is incorporated herein by reference. In general, the blood pump is generally similar to the blood pumps described in WO 14/141284 to Schwammenthal, WO 15/177793 to Schwammenthal, and/or WO 16/185473 to Schwammenthal, all of which are incorporated herein by reference.

For some applications, one or more blood pressure sensors 68, 70, and/or 72 are disposed on catheter 66, respectively, downstream of pump 60, between pump 60 and nozzle 50, and upstream of nozzle 50. Thus, the blood pressure measured by blood pressure sensor 68 is indicative of central venous pressure, the blood pressure measured by blood pressure sensor 70 is indicative of renal venous pressure, and the blood pressure measured by blood pressure sensor 72 is indicative of lower-body venous pressure. For some applications, a control unit modulates the pumping of the blood by pump 60 responsively to the pressure measured by one or more of the pressure sensors, for example, as described in WO 14/141284 to Schwammenthal, WO 15/177793 to Schwammenthal, and/or International Patent Application WO 16/185473 to Schwammenthal, all of which are incorporated herein by reference. The control unit is typically a computer processor 69 that includes hardware components.

For some applications, the extent to which nozzle 50 occludes the vena cava is controllable. For example, as shown the nozzle may be constructed from a frame 56 (which is typically made of a shape-memory material, such as nitinol) and a blood-impermeable material 58 (e.g., polyester, polyurethane, and/or a different polymer) that is supported by the frame. The frame of the nozzle may be expandable (e.g., by heating the frame, or by applying an electrical current to the frame), such that the diameter of the opening defined by the nozzle is controllable. For some applications, the extent to which nozzle 50 occludes the vena cava is modulated by a control unit (e.g., control unit 69), responsively to blood pressure measurements that are measured by blood pressure sensor 68, 70, and/or 72. The control unit is typically a computer processor (e.g., computer processor 69) that includes hardware components. For some applications, a nozzle that is controllable such that the diameter of the opening defined by the nozzle may be modulated as described in the present paragraph, is used even in the absence of blood pump 60. For example, in the configurations shown in FIGS. 3 and 4, nozzle 50 and/or nozzle 52 may be controllable such that the diameter of the opening defined by the nozzle may be modulated, as described in the present paragraph.

For some applications, nozzle 50 is used in the absence of both nozzle 52 and blood pump 60. Typically, the nozzle is configured to partially occlude the subject's vena cava such as to reduce the subject's central venous pressure. Alternatively or additionally, due the convergence of nozzle 50, blood flowing through the nozzle undergoes the venturi effect, thereby adding to the reduction in pressure within region 54, relative to central venous pressure. Typically, by generating a region of low pressure, blood flow from the renal veins into the vena cava increases, thereby lowering renal blood pressure and enhancing renal perfusion. For some such applications, nozzle 50 is controllable by a control unit, such that the diameter of the opening defined by the nozzle may be modulated. Typically, the control unit is a computer processor (e.g., computer processor 69) that includes hardware components. For example, the control unit may modulate the diameter of the opening defined by the nozzle responsively to blood pressure measurements that are measured by blood pressure sensor 68, 70, and/or 72.

Although FIG. 5 shows the blood pump and the nozzle disposed on a catheter that is inserted into the vena cava from above the junctions of the vena cava with the subject's renal veins (e.g., via the subject's subclavian vein or jugular vein), for some applications, the blood pump and the nozzle are disposed on a catheter that is inserted into the vena cava from below the junctions of the vena cava with the subject's renal veins (e.g., via the subject's femoral vein), mutatis mutandis. Alternatively or additionally, the nozzle is disposed on a first catheter which is inserted into the vena cava from below the junctions of the vena cava with the subject's renal veins (e.g., via the subject's femoral vein), and the blood pump is disposed on a second catheter, which inserted into the vena cava from above the junctions of the vena cava with the subject's renal veins (e.g., via the subject's subclavian vein, or jugular vein).

Although blood pump 60 is described as being an impeller-based pump, the scope of the present invention includes using any other type of pump for pumping blood in the manner described herein, mutatis mutandis. For example, a roller pump, an Archimedes screw pump, a centrifugal pump, a pneumatic pump, and/or a compression pump may be used.

Typically, the apparatus shown in FIG. 5 is used to apply an acute treatment to the subject, in order to treat the subject for one or more of the conditions described herein.

Figure 6:
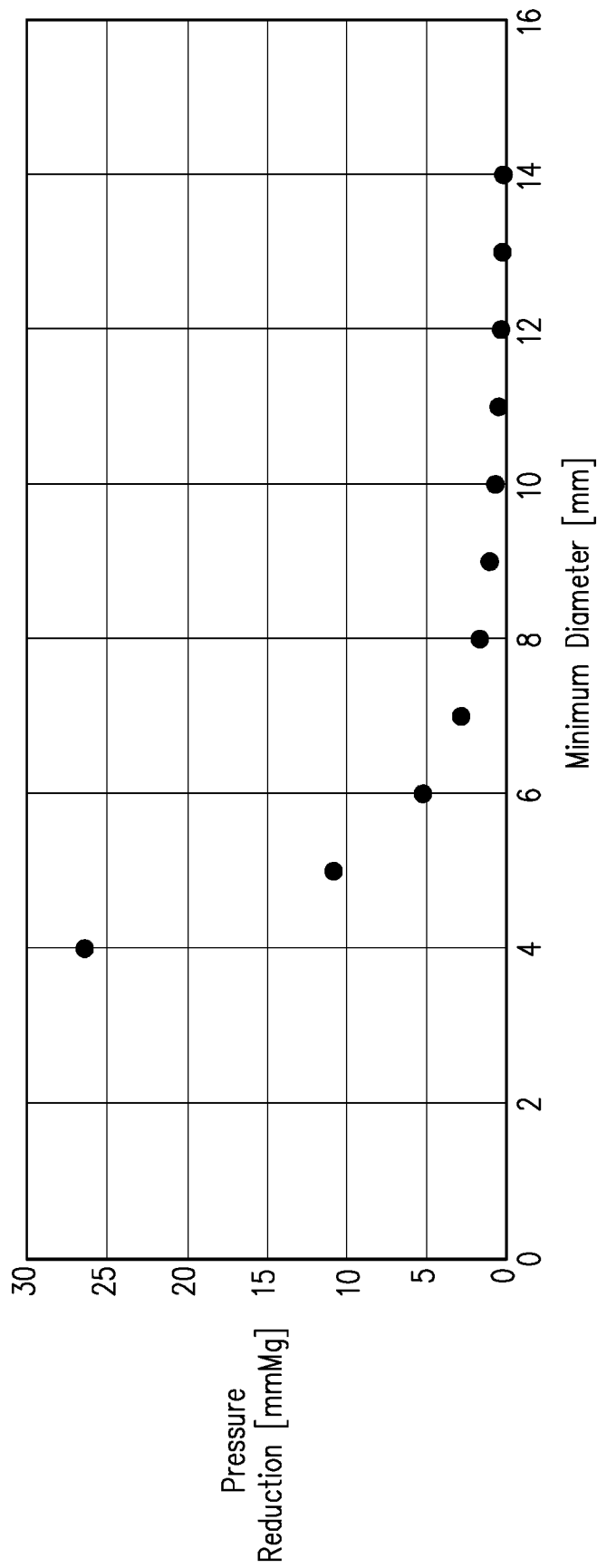
FIG. 6 is a graph showing the results of calculations that were performed to model the effects of placing a venturi tube inside a subject's vena cava, in accordance with some applications of the present invention.

Reference is now made to FIG. 6, which is a graph showing the results of calculations that were performed to model blood flowing through the renal veins and the vena cava via a venturi tube having characteristics generally as described herein with reference to FIGS. 1 and 2. Pressure reduction within the renal veins was calculated for tubes having respective minimum inner diameters. FIG. 6 shows the pressure reduction that was calculated for the venturi tubes having the respective inner diameters.

It may be observed that as the minimum inner diameter is reduced the resultant pressure reduction within the renal veins is greater (i.e., the pressure within the renal veins is reduced by increasing amounts). These results indicate that techniques as described herein may cause a reduction in renal venous pressure, and that reducing the minimum inner diameter of the venturi tube (or of the nozzle, for applications as described with reference to FIGS. 3 and 4) may cause a greater reduction in the renal venous pressure. It is noted that there is a lower limit to the minimum inner diameter of the tube or the nozzle that can be used, due to the fact that below a given minimum diameter, the drag force that would be generated by the tube (or the nozzle) on the blood flow through the tube (or the nozzle) would impede blood flow via the tube (or the nozzle), which would reduce blood flow toward the heart via the vena cava, thereby endangering the patient. The inventors hypothesize that the lower limit for the minimum diameter of the tube or the nozzle is 3 mm.

Therefore, as described hereinabove, typically, (in its non-constrained configuration) inner diameter D2 of the tube at the location at which the inner diameter is at its minimum (which is typically toward the longitudinal center of the tube) is greater than 3 mm (e.g., greater than 4 mm) and/or less than 8 mm (e.g., less than 6 mm), e.g., 3-8 mm, or 4-6 mm. Similarly, the minimum diameter of the nozzle (i.e., the diameter at the tip of the nozzle) is typically greater than 3 mm (e.g., greater than 4 mm) and/or less than 8 mm (e.g., less than 6 mm), e.g., 3-8 mm, or 4-6 mm.

For some applications, venturi tube 20 is configured such that the minimum inner diameter of the tube may be modulated, for example, by constructing the tube in a similar manner to that described with reference to nozzle 50 as shown in FIG. 5, and using techniques as described with reference to nozzle 50 as shown in FIG. 5, mutatis mutandis. For some such applications, the minimum inner diameter of the tube is modulated by a control unit. Typically, the control unit is a computer processor (e.g., computer processor 69, shown in FIG. 5) that includes hardware components. For example, the control unit may modulate the minimum inner diameter of the tube responsively to blood pressure measurements that are indicative of central venous pressure, renal venous pressure, and/or lower-body venous pressure, as described hereinabove, with reference to blood pressure sensor 68, 70, and/or 72. It is noted that venturi tube 20, nozzles 50 and 52, and blood pump 60 are generally described as being placed within the subject's vena cava in the vicinity of the junctions of the renal veins with the vena cava. However, the scope of the present invention includes placing venturi tube 20, nozzles 50 and 52, and/or blood pump 60 in any vein that has junctions with a tributary vessel, in accordance with the techniques described herein, mutatis mutandis. For example, venturi tube 20, nozzles 50 and 52, and/or blood pump 60 may be placed within the vena cava in the vicinity of junctions of the vena cava with the subject's hepatic veins, and may be used to increase blood flow from the subject's hepatic veins into the subject's vena cava, in order to increase perfusion of the subject's liver, mutatis mutandis. Alternatively or additionally, venturi tube 20, nozzles 50 and 52, and/or blood pump 60 could be placed within the subclavian vein or jugular vein at junctions of the vein with a lymph duct and could be used to increase flow of lymphatic fluid from the lymph duct into the vein, mutatis mutandis.

The scope of the present invention includes combining any of the apparatus and methods described herein with any of the apparatus and methods described in one or more of the following applications, all of which are incorporated herein by reference:

International Patent Application PCT/IL2016/050525 to Schwammenthal (published as WO 16/185473), filed May 18, 2016, entitled "Blood pump," which U.S. Provisional Patent Application 62/162,881 to Schwammenthal, filed May 18, 2015, entitled "Blood pump;"

International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. patent application Ser. No. 14/567,439 to Tuval (issued as U.S. Pat. No. 9,764,113), filed Dec. 11, 2014, entitled "Curved catheter," which claims priority from U.S. Provisional Patent Application 61/914,470 to Tuval, filed Dec. 11, 2013, entitled "Curved catheter;" and International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

There is therefore provided, in accordance with some applications of the present invention, the following inventive concepts:

Inventive concept 1. A method for use with renal veins and a vena cava of a subject, the method comprising:

placing a nozzle in the subject's vena cava upstream of junctions of the vena cava with all of the subject's renal veins, such that the first nozzle converges in a direction of antegrade blood flow through the vena cava;

placing a blood pump in the subject's vena cava downstream of the junctions of the vena cava with all of the subject's renal veins; and operating the blood pump to blood pump in direction of antegrade blood flow through the vena cava.

Inventive concept 2. Apparatus for use with renal veins and a vena cava of a subject, the apparatus comprising:

a nozzle configured to be placed in the subject's vena cava upstream of junctions of the vena cava with all of the subject's renal veins, such that the first nozzle converges in a direction of antegrade blood flow through the vena cava; and a blood pump configured to be placed in the subject's vena cava downstream of the junctions of the vena cava with all of the subject's renal veins, and to blood pump in the direction of antegrade blood flow through the vena cava.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with renal veins and a vena cava of a subject, the apparatus comprising:

a tube that defines:

a flared downstream portion thereof that diverges toward a downstream end of the tube, and a flared upstream portion thereof that diverges toward an upstream end of the tube, such that a narrow central portion of the tube is narrower than at the ends of the tube, and a plurality of lateral openings; and a support frame configured to support the tube within the subject's vena cava, such that:

the downstream portion of the tube is sealed with respect to an inner wall of the vena cava at a location that is downstream of junctions of the vena cava with all of the subject's renal veins, and the upstream portion of the tube is sealed with respect to the inner wall of the vena cava at a location that is upstream of junctions of the vena cava with all of the subject's renal veins, wherein the tube is configured to generate a region of low pressure within the narrow central portion, by blood flowing from the upstream end of the tube and through the narrow central portion of the tube, the tube thereby being configured to reduce renal venous pressure of the subject by drawing blood from the subject's renal veins into the low pressure region via the lateral openings.

2. The apparatus according to claim 1, wherein the plurality of lateral openings are shaped such as to converge toward a longitudinal axis of the tube.

3. The apparatus according to claim 1, wherein an inner diameter of the tube at a location at which the inner diameter is at its maximum is greater than 12 mm.

4. The apparatus according to claim 1, wherein an inner diameter of the tube at a location at which the inner diameter is at its minimum is less than 8 mm.

5. The apparatus according to claim 1, wherein a ratio between an inner diameter of the tube at a location at which the inner diameter is at its maximum and an inner diameter of the tube at a location at which the inner diameter is at its minimum is greater than 3:1.

6. The apparatus according to claim 1, wherein a length of the tube is greater than 20 mm.

7. The apparatus according to claim 1, further comprising:
one or more blood pressure sensors configured to measure blood pressure within the vena cava; and
a computer processor configured to modulate a diameter of the central portion of the tube responsively to the measured blood pressure.

8. The apparatus according to claim 7, wherein the one or more blood pressure sensors are configured to measure an indication of renal venous pressure of the subject.

9. The apparatus according to claim 7, wherein the one or more blood pressure sensors are configured to measure an indication of central venous pressure of the subject.

10. The apparatus according to claim 7, wherein the one or more blood pressure sensors are configured to measure an indication of lower-body venous pressure of the subject.

11. The apparatus according to claim 1, wherein a ratio between an inner diameter of the tube at the upstream end of the tube and an inner diameter of the tube within the narrow central portion is greater than 3:1.

12. A method for use with renal veins and a vena cava of a subject, the method comprising:
providing a tube that defines:
a flared downstream portion thereof that diverges toward a downstream end of the tube, and a flared upstream portion thereof that diverges toward an upstream end of the tube, such that a narrow central portion of the tube is narrower than at the ends of the tube, and
a plurality of lateral openings; and
placing the tube within the subject's vena cava, such that:
the downstream portion of the tube is sealed with respect to an inner wall of the vena cava at a location that is downstream of junctions of the vena cava with all of the subject's renal veins, and the upstream portion of the tube is sealed with respect to the inner wall of the vena cava at a location that is upstream of junctions of the vena cava with all of the subject's renal veins, the tube generates a region of low pressure within the narrow central portion, by blood flowing from the upstream end of the tube and through the narrow central portion of the tube, and the tube thereby reduces renal venous pressure of the subject by drawing blood from the subject's renal veins into the low pressure region via the lateral openings.

13. The method according to claim 12, wherein providing the tube comprises providing the tube, the plurality of lateral openings being shaped such as to converge toward a longitudinal axis of the tube.

14. The method according to claim 12, wherein providing the tube comprises providing the tube, an inner diameter of the tube at a location at which the inner diameter is at its maximum being greater than 12 mm.

15. The method according to claim 12, wherein providing the tube comprises providing the tube, an inner diameter of the tube at a location at which the inner diameter is at its minimum being less than 8 mm.

16. The method according to claim 12, wherein providing the tube comprises providing the tube, a ratio between an inner diameter of the tube at a location at which the inner diameter is at its maximum and an inner diameter of the tube at a location at which the inner diameter is at its minimum being greater than 3:1.

17. The method according to claim 12, wherein providing the tube comprises providing the tube, a length of the tube being greater than 20 mm.

18. The method according to claim 12, further comprising:
measuring blood pressure within the vena cava; and
modulating a diameter of the central portion of the tube responsively to the measured blood pressure.

19. The method according to claim 18, wherein measuring blood pressure within the vena cava comprises measuring an indication of renal venous pressure of the subject.

20. The method according to claim 18, wherein measuring blood pressure within the vena cava comprises measuring an indication of central venous pressure of the subject.

21. The method according to claim 18, wherein measuring blood pressure within the vena cava comprises measuring an indication of lower-body venous pressure of the subject.

22. The method according to claim 12, further comprising identifying the subject as suffering from a condition selected from the group consisting of: cardiac dysfunction, congestive heart failure, reduced renal blood flow, increased renal vascular resistance, arterial hypertension, diabetes, and kidney dysfunction, wherein placing the tube within the subject's vena cava comprises placing the tube within the subject's vena cava, in response to identifying the subject as suffering from the selected condition.

23. The method according to claim 22, wherein placing the tube within the subject's vena cava comprises treating the selected condition by reducing renal venous pressure of the subject.

24. Apparatus for use with renal veins and a vena cava of a subject, the apparatus comprising:
a tube that defines:
a flared downstream portion thereof that diverges toward a downstream end of the tube, and a flared upstream portion thereof that diverges toward an upstream end of the tube, such that a central portion of the tube is narrower than at the ends of the tube, and a plurality of lateral openings;

a support frame configured to support the tube within the subject's vena cava, such that:

the downstream portion of the tube is sealed with respect to an inner wall of the vena cava at a location that is downstream of junctions of the vena cava with all of the subject's renal veins, and the upstream portion of the tube is sealed with respect to the inner wall of the vena cava at a location that is upstream of junctions of the vena cava with all of the subject's renal veins;

one or more blood pressure sensors configured to measure blood pressure within the vena cava; and a computer processor configured to modulate a diameter of the central portion of the tube responsively to the measured blood pressure.

25. A method for use with renal veins and a vena cava of a subject, the method comprising:

providing a tube that defines:

a flared downstream portion thereof that diverges toward a downstream end of the tube, and a flared upstream portion thereof that diverges toward an upstream end of the tube, such that a central portion of the tube is narrower than at the ends of the tube, and a plurality of lateral openings;

placing the tube within the subject's vena cava, such that:

the downstream portion of the tube is sealed with respect to an inner wall of the vena cava at a location that is downstream of junctions of the vena cava with all of the subject's renal veins, and the upstream portion of the tube is sealed with respect to the inner wall of the vena cava at a location that is upstream of junctions of the vena cava with all of the subject's renal veins;

measuring blood pressure within the vena cava; and modulating a diameter of the central portion of the tube responsively to the measured blood pressure.

* * * * *